(12) United States Patent
Miyazaki et al.

(10) Patent No.: US 9,193,010 B2
(45) Date of Patent: Nov. 24, 2015

(54) DEVICE AND METHODS FOR TESTING QUALITY OF WELDING JOINTS

(71) Applicant: EMBRAER S.A., São José dos Campos/SP (BR)

(72) Inventors: Marcos Hideki Miyazaki, São José dos Campos/SP (BR); Marcos Antonio Batista Goncalves, São José dos Campos/SP (BR); Andreza Sommerauer Franchim Viliotti, São José dos Campos/SP (BR); Fernando Ferreira Fernandez, São José dos Campos/SP (BR)

(73) Assignee: EMBRAER S.A., São José dos Campos—SP (BR)

( * ) Notice: Subject to any disclaimer, the term of this patent is extended or adjusted under 35 U.S.C. 154(b) by 171 days.

(21) Appl. No.: 13/955,189

(22) Filed: Jul. 31, 2013

(65) Prior Publication Data

US 2014/0157862 A1  Jun. 12, 2014

Related U.S. Application Data

(60) Provisional application No. 61/679,362, filed on Aug. 3, 2012.

(51) Int. Cl.
*B23K 31/12* (2006.01)
*G01N 3/00* (2006.01)
*B23K 20/12* (2006.01)

(52) U.S. Cl.
CPC ............. *B23K 31/125* (2013.01); *B23K 20/122* (2013.01); *G01N 3/00* (2013.01); *G01N 2203/0296* (2013.01)

(58) Field of Classification Search
CPC ........ B23K 31/125; B23K 2/122; G01N 3/30; G01N 2203/0296
USPC ............................................ 73/850, 856, 845
See application file for complete search history.

(56) References Cited

U.S. PATENT DOCUMENTS 5,394,754 A * 3/1995 Herring, Jr. ...................... 73/826
8,301,307 B2 * 10/2012 Paulus et al. ................... 700/282

* cited by examiner

*Primary Examiner* — Lisa Caputo
*Assistant Examiner* — Tran M Tran
(74) *Attorney, Agent, or Firm* — Nixon & Vanderhye P.C.

(57) ABSTRACT

Devices and methods are provided for testing weld strengths of a test coupon joint. A test coupon is positionally fixed to a base of the testing device. A punch assembly having a head portion is provided so as to exert an axial force against an upright part of the test coupon to thereby determine weld strength between the planar and upright parts of the test coupon (e.g., a maximum force at which weld failure occurs).

16 Claims, 4 Drawing Sheets

DEVICE AND METHODS FOR TESTING QUALITY OF WELDING JOINTS

CROSS-REFENCE TO RELATED APPLICATION

The present application is based on and claims domestic priority benefits under 35 USC §119(e) from U.S. Provisional Patent Application Ser. No. 61/679,362 filed on Aug. 3, 2012, the entire content of which is expressly incorporated hereinto by reference.

FIELD

The embodiments disclosed herein relate generally to devices and methods for testing the quality of weld strengths, especially the strength of welding joints formed by friction stir welding (FSW) techniques.

BACKGROUND AND SUMMARY

Friction stir welding (FSW) is commonly used to weld two or more work pieces formed of various metals, such as aluminum, magnesium, copper, titanium, steel and the like, one to another. FSW techniques may be employed satisfactorily to form welded lap joint, L-joint and/or T-joint.

During conventional FSW processes (including continuous and segmented friction stir welding), a FSW tool having a specific geometry is forced into, and traversed through the material to be welded. The key structural components of the tool include a shoulder and pin (sometimes called a "probe" in art parlance) extending outwardly from the shoulder. During the FSW process, the pin travels physically in and through the material along a joint line, while the shoulder is in surface contact with the material. Heat is generated by the tool shoulder by virtue frictional rubbing on the material surface it is in contact with and by virtue of the pin mixing the softened material below the shoulder. This mixing action of the softened material during the FSW process permits the material to be transferred across the joint line which forms a stirred region. Process variables affecting the FSW process may include rotation and travel speeds, tool design, orientation, position and tool forging load. Conventional FSW processes are disclosed, for example, by U.S. Pat. Nos. 7,225,966 and 7,240,821 (the entire contents of which are expressly incorporated hereinto by reference.

There is currently no known shop floor testing device or method near a FSW machine whereby welding parameters may be rapidly assessed in order to evaluate the quality of the weld. Instead, according to current practices, in order to analyze the quality of the welded joint during a research and development phase, several sets of FSW parameters (for example, welding speed, rotation speed and axial force) are established. A number of test specimens (coupons) formed of FSW welded components are thereafter produced in accordance with each set of FSW parameters in order to evaluate the welding quality associated with each set of parameters. Off-line testing such as metallography, tensile and pull-out tests are typically performed before selecting the set of FSW parameter for a given design criteria. As can be appreciated, this conventional iterative process is quite time consuming and is therefore quite expensive.

It would therefore be desirable if devices and methods were provided locally at a friction stir or other welding machine which could more easily and economically enable a manufacturer to verify and test the quality of welding joint strengths on coupons. It is towards providing such devices and methods that the embodiments disclosed herein are directed.

According to certain embodiments as disclosed herein, a device for testing weld strength of a test coupon joint is provided which includes a base defining a receiving region to receive and support a lower part of the test coupon and a clamp for positionally fixing the lower part of the test coupon to the base. A punch assembly having a head portion is provided so as to exert an axial force against the upright part of the test coupon to thereby determine weld strength between the planar and upright parts of the test coupon. A U-shaped receiver can be fixed to the base to define the receiving region. The base may include a rearward projecting portion to provide attachment and support for the clamping assembly.

The punch assembly may include a tail portion axially extending from the head portion for connection to a force actuator. According to some embodiments, the punch assembly may include a clamp piece connected to the head portion of the punch assembly for axial adjustments relative to a front face of the head portion so as to clamp the upright part of the test coupon thereagainst.

A guide assembly is provided according to certain embodiments and is removably connected to the base. The guide assembly in some embodiments will define a guideway for the tail portion of the punch assembly to allow for reciprocal axial movements thereof. The guideway will thus positionally capture the tail portion of the punch assembly to allow only axial movements thereof towards and away from the upright part of the test coupon. According to some embodiments, the base may include a forward projecting portion so that the guide assembly may be removably connected thereto. Certain embodiments of the device will be provided with a guide assembly comprised of opposed end blocks and a bridge section connected to and spanning the distance between the end blocks.

According to another aspect of the invention, a method is provided whereby the weld strength of a joint of a test coupon may be tested. In general, such a method will include clamping the lower part of the test coupon to a base of a testing device, moving a punch assembly of the testing device to exert an axial force against the upright part of the test coupon, and determining a maximum force of weld failure between the planar and upright parts of the test coupon.

According to some embodiments, the method may include providing a guide assembly which defines a guideway for positionally capturing a tail portion of the punch assembly to allow only axial movements thereof towards and away from the upright part of the test coupon. A clamp piece may be positioned relative to a front face of the head portion to clamp the upright part of the test coupon against the front face of the head portion. Such claim piece may be axially adjusted so as to positionally clamp the upright part of the test coupon against the front face of the head portion.

These and other aspects and advantages of the present invention will become more clear after careful consideration is given to the following detailed description of the preferred exemplary embodiments thereof.

BRIEF DESCRIPTION OF ACCOMPANYING DRAWINGS

The disclosed embodiments of the present invention will be better and more completely understood by referring to the following detailed description of exemplary non-limiting illustrative embodiments in conjunction with the drawings of which:

DETAILED DESCRIPTION

Figure 1:
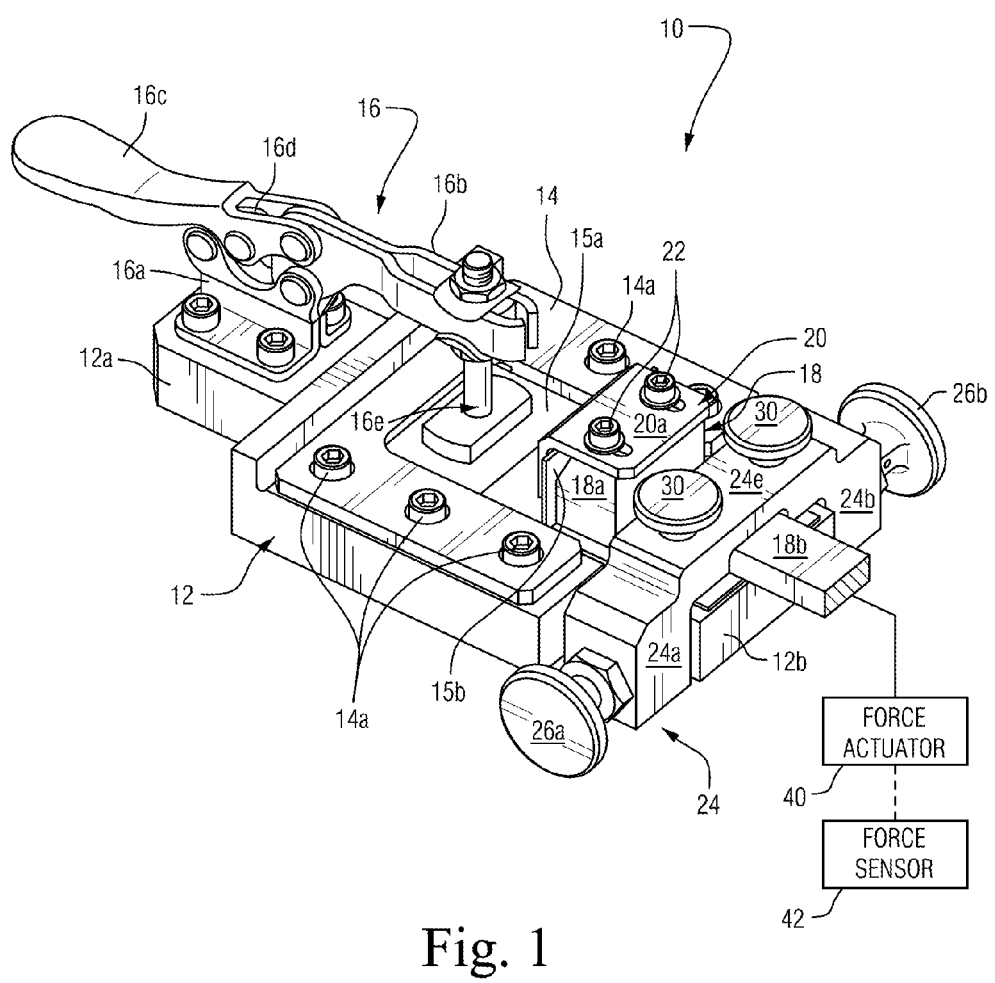
FIG. 1 is a top perspective view of a device in accordance with an embodiment of the present invention for testing the quality of bond strengths of friction stir welded coupons.

Accompanying FIG. 1 shows an assembly view of a testing device 10 in accordance with an embodiment of the present invention for testing the quality of bond strengths of friction stir welded coupons. Specifically, the device 10 includes a base 12 having a generally U-shaped coupon receiver 14 fixed to an upper face thereof (e.g., by means of bolts 14a). The coupon receiver 14 is thereby adapted to receive the lower part 15a of a test specimen (coupon) 15. As shown, the lower part 15a is in a planar surface having an upper L-shaped part 15b bonded thereto by FSW so that an upright portion of the L-shaped part 15b is essentially at a right angle to the lower planar part 15a (see FIG. 2). Alternatively, the lower part 15a may have a non-planar surface geometry, e.g., in the form of a curved surface. In such a case, a corresponding region of the upper face of the base 12 would then likewise be curved so as to conformably match the curved surface of the lower part 15a.

The base 12 includes a rearward projecting portion 12a to which a clamping assembly 16 is attached. The clamping assembly 16 includes a clamp support 16a fixed to the projecting portion 12a of base 12, a forward finger assembly 16b pivotally connected to the clamp support 16a and a manually actuated handle member 16c pivotally attached to the finger assembly 16b at a distal end and being pivotally connected proximally to the clamp support 16a by means of a linkage 16d. The distal end of the finger assembly 16b carries a vertically adjustable clamp foot assembly 16e. By manipulating the handle member 16c between lowered and raised positions will thereby in turn responsively move the the finger assembly 16b, and hence the clamp foot assembly 16e, respectively between an unclamped condition (wherein the test coupon 15 is not immovably clamped to the base 12) and a clamped condition (wherein the test coupon 15 is immovably clamped to the base 12).

Figure 2:
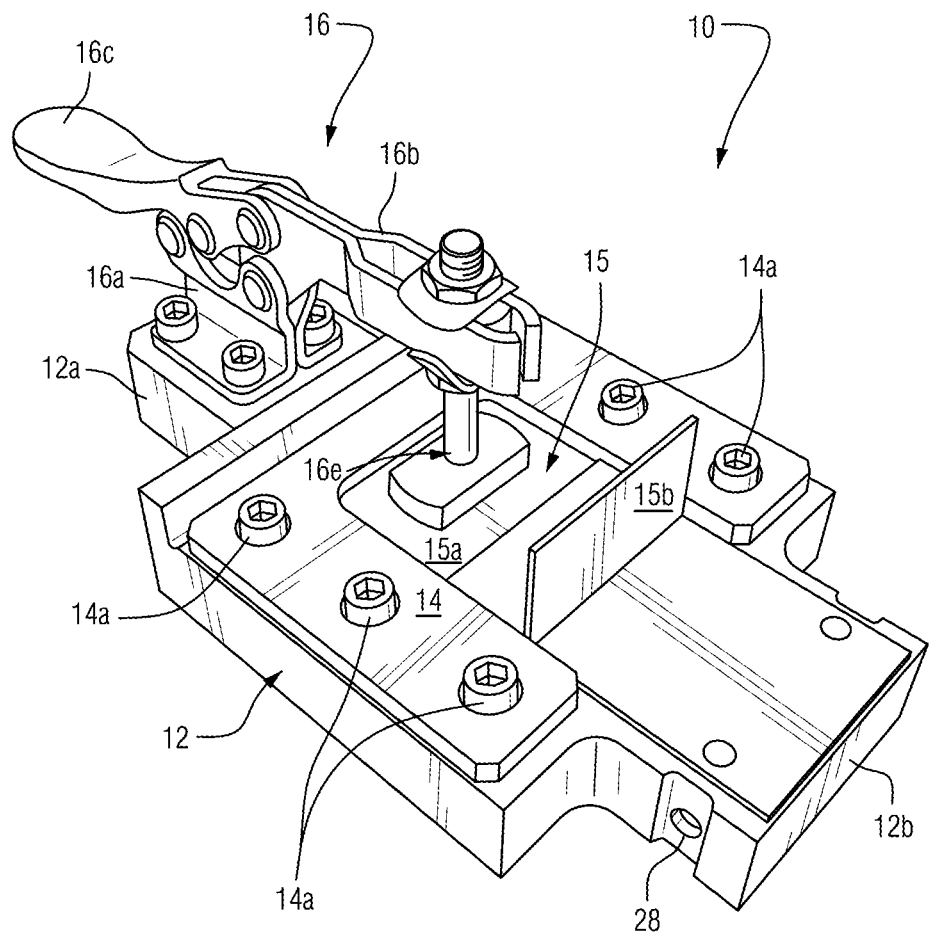
FIG. 2 is top perspective view of the device depicted in FIG. 1 without the removable guide component thereof.
Figure 3:
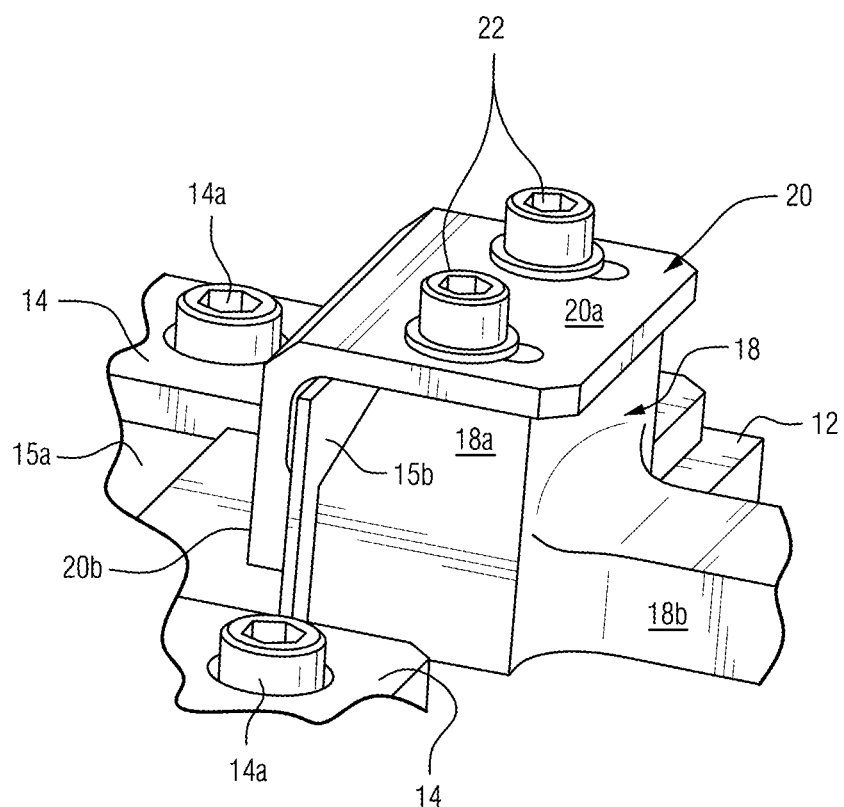
FIG. 3 is a detailed perspective view of a punch assembly employed in the device of FIG. 1.
Figure 4:
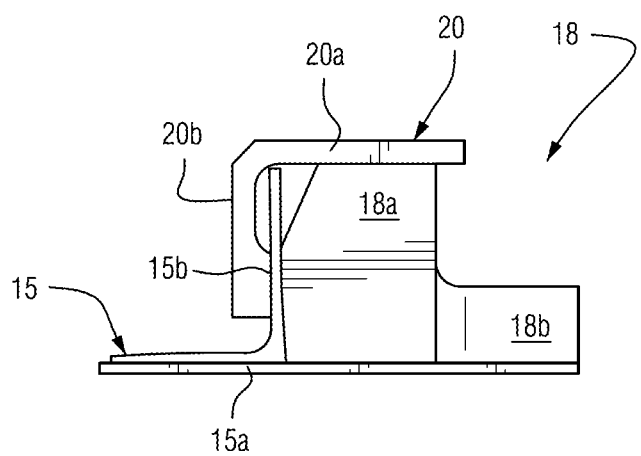
FIG. 4 is a simplified elevational view of the punch assembly shown in FIG. 3.

As shown by FIG. 2, the end of the base 12 opposite the projecting portion 12a includes a forward projecting portion 12b. An axial punch assembly 18 is provided having a head portion 18a abutted against the upright portion of the L-shaped part 15b and a tail portion 18b extending therefrom. As is perhaps best shown by FIGS. 3 and 4, the head portion 18a carries an axially adjustable L-shaped clamp piece 20 having a top flange 20a adjustably fixed to the head portion 18a by means of bolt assemblies 22. The bottom flange 20b of the clamp piece 20 extends over a portion of the upright portion of the L-shaped part 15b so as to securely clamp such portion against the front face of the head portion 18a of the axial punch assembly 18.

Figure 5:
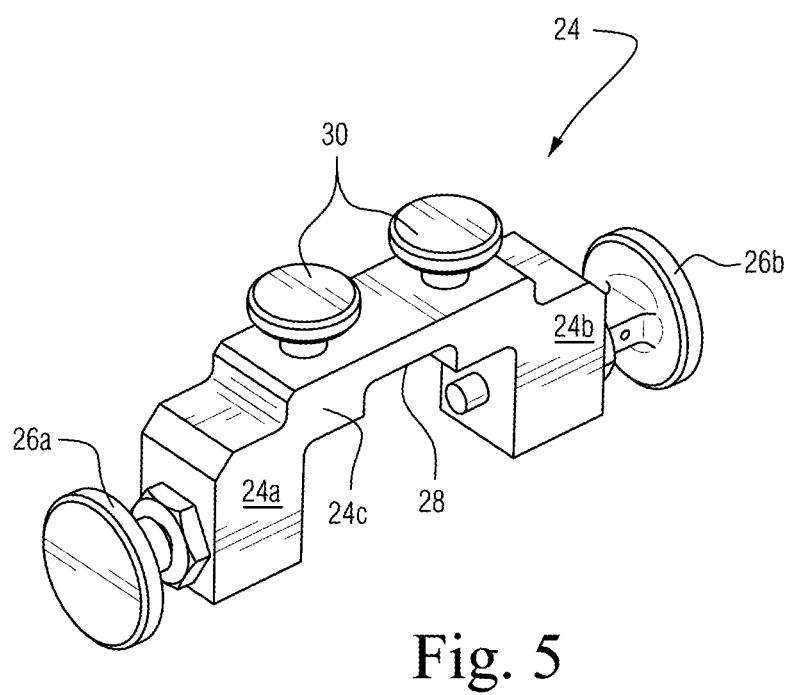
FIG. 5 is a detailed perspective view of the removable guide component employed in the device of FIG. 1.

A removable guide assembly 24 is provided so as to be removably coupled to the forward projecting portion 12b. As shown by FIG. 5, the removable guide assembly is generally an inverted U-shaped structure having opposed end blocks 24a, 24b and a bridge section 24c which spans the distance therebetween. Retaining bolt assemblies 26a, 26b are operatively provided with each end block 24a, 24b, respectively, so as to immovably attach the guide assembly 24 to the forward projecting portion 12b of the base 12 (e.g., via respective threaded apertures 28 formed therein (see FIG. 2). The lower surface of the bridge section 24c defines a guide recess 28 sized and configured to accept therein the tail portion 18b of the punch assembly 18. A pair of threaded blank holders 30 may also be provided so as to enhance the holding capability for positionally fixing the lower part 15a of the coupon 15 to the base 12.

In use, a test coupon 15 is placed in the coupon receiver 14 and clamped to the base 12 by means of the clamping assembly 16. The punch assembly may then be positioned on the device so the head 18a is abutted against the upright portion of the L-shaped part 15b. The axially adjustable (i.e., relative to the elongate axis of the tail portion 18b) L-shaped clamp piece 20 may then be positioned and fixed to the head portion 18a so as to immovably fix the upright portion of the L-shaped part 15b therebetween. Thereafter, the removable guide assembly 24 is installed and fixed to the forward projecting portion 12b of the base 12 thereby capturing the tail portion 18b of the punch assembly 18 in the guide recess 28 thereof. In such a manner, it is assured that only an axial force coplanar with the lower part 15a of the coupon 15 but perpendicular to the plane of the upper part 15b is applied against the upper part 15b thereof. As such, bending of the upper part 15b is prevented so that the force that is transmitted by the punch assembly to the upright part 15b of the test coupon 15 is focused on the weld between such upright part 15b and the lower part 15a thereof (i.e., the weld joint formed in the flange of the L-shaped part 15b which is abutted against and coplanar with the lower part 15a).

The tail portion 18b of the punch assembly 18 may be connected to a suitable force actuator, for example a hydraulic ram-type actuator (shown schematically in FIG. 1 by reference numeral 40) so that progressive axial force may be applied against the upright part 15b of the test coupon 15 until such time as the weld between the parts 15a and 15b fails. A sensor, such as a digital or analog manometer (shown schematically in FIG. 1 by reference numeral 42) can be employed to monitor the applied force until weld failure occurs, following which the maximum force of the weld at failure can be recorded (e.g., either manually using a drag pointer or electronically using suitable computer-aided means). The result obtained by such testing may then be compared with a value previously obtained with a standard specimen with known good mechanical properties. If the result is not satisfactory, the part is rejected. If however the result is satisfactory, the welding parameters are validated and considered for further testing.

\* \* \*

Various modifications within the skill of those in the art may be envisioned. Therefore, while the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope thereof.

What is claimed is:

1. A testing device for testing weld strength of a joint of a test coupon having a lower part and an upright part welded to the lower part, the device comprising:

a base to support the lower part of the test coupon such that the upright part extends upwardly from the base;

a U-shaped receiver fixed to the base which defines a receiving region to receive the lower part of the test coupon;

a clamp assembly for positionally fixing the lower part of the test coupon received within the U-shaped receiver to the base;

a punch assembly having a head portion defining a front face, and an L-shaped clamp piece having a top flange adjustably connected to the head portion of the punch assembly and a bottom flange extending over a portion of the upright part of the test coupon so as to clamp the upright part of the test coupon between the bottom flange of the clamp piece and the front face of the head portion, wherein the punch assembly is axially movable relative to the upright part of the test coupon so as to cause the head portion to exert an axial force against the upright part of the test coupon to thereby test weld strength of a joint between the lower and upright parts of the test coupon.

2. The device of claim 1, wherein the punch assembly comprises a tail portion for connection to a force actuator.

3. The device of claim 2, wherein the clamp piece is connected to the head portion of the punch assembly for axial adjustments relative to the front face of the head portion.

4. The device of claim 2, further comprising a guide assembly removably connected to the base and defining a guideway for the tail portion of the punch assembly to allow for reciprocal axial movements thereof.

5. The device of claim 1, wherein the base includes a rearward projecting portion, and wherein the clamping assembly is attached to and supported by the rearward projecting portion.

6. The device of claim 1, wherein the base includes a forward projecting portion, and wherein the device further includes a guide assembly removably connected to the forward projecting portion, the guide assembly defining a guideway for the punch assembly to allow for axial movements thereof.

7. The device of claim 6, wherein the punch assembly includes an elongate tail portion axially extending from the head portion thereof, and wherein the guide assembly defines a guideway for positionally capturing the tail portion to allow only axial movements thereof towards and away from the upright part of the test coupon.

8. The device of claim 1, comprising a guide assembly removably connected to the base to positionally restrain the punch assembly and provide for axial movements thereof towards and away from the upright portion of the test coupon.

9. The device of claim 8, wherein the guide assembly comprises opposed end blocks and a bridge section connected to and spanning a distance between the end blocks.

10. The device of claim 9, wherein the punch assembly comprises a tail portion axially extending from the head portion, and wherein the bridge section of the guide assembly defines a guideway through which the tail portion is positioned.

11. The device of claim 1, further comprising an actuator operatively connected to the punch assembly so as to cause the head portion of the punch assembly to exert an axial force against the upright part of the test coupon, and a force sensor for determining a maximum force of weld strength failure.

12. A method for testing weld strength of a joint of a test coupon having a lower part and an upright part welded to the lower part, the method comprising the steps of:

(a) providing a testing device according to claim 1;

(b) clamping the lower part of the test coupon to the base of the testing device;

(c) moving the punch assembly of the testing device to cause the head portion thereof to exert an axial force against the upright part of the test coupon; and (d) determining a maximum force of weld failure between the lower and upright parts of the test coupon.

13. The method according to claim 12, wherein the punch assembly includes an elongate tail portion axially extending from the head portion thereof, and wherein the method includes providing a guide assembly which defines a guideway for positionally capturing the tail portion to allow only axial movements thereof towards and away from the upright part of the test coupon.

14. The method according to claim 12, which comprises positioning the L-shaped clamp piece relative to the front face of the head portion to clamp the upright part of the test coupon against the front face of the head portion.

15. The method according to claim 14, which comprises axially adjusting the clamp piece to positionally clamp the upright part of the test coupon against the front face of the head portion.

16. The method according to claim 13, wherein the base includes a forward projecting portion, and wherein the method further comprises removably connecting the guide assembly to the forward projecting portion.

* * * * *